United States Patent [19]

Nielsen et al.

[11] Patent Number: 5,071,276
[45] Date of Patent: Dec. 10, 1991

[54] CONTACT LENS CLEANING SYSTEM

[75] Inventors: Randolph D. Nielsen, Worthington, Ohio; Gerald W. Hietala, Danville, Calif.; Clarence J. Endicotti, Libertyville, Ill.

[73] Assignee: Abbott Laboratories, Abbott Park, Ill.

[21] Appl. No.: 637,585

[22] Filed: Jan. 4, 1991

[51] Int. Cl.$^5$ ............................................. G02C 13/00
[52] U.S. Cl. .................................... 401/9; 15/214; 206/5.1; 401/11; 401/48; 401/196
[58] Field of Search ................ 401/9, 10, 11, 196, 401/48; 15/214; 206/5.1

[56] References Cited

U.S. PATENT DOCUMENTS

| | | | |
|---|---|---|---|
| 2,227,710 | 1/1941 | Finn | 15/214 X |
| 3,087,189 | 4/1963 | Scanlon | 401/11 |
| 3,822,780 | 7/1974 | Ulmer et al. | 206/5.1 |
| 4,357,173 | 11/1982 | Rosenthal et al. | 206/5.1 X |
| 4,559,662 | 12/1985 | Kunold, Jr. | 15/214 X |

FOREIGN PATENT DOCUMENTS

| | | | |
|---|---|---|---|
| 2701016 | 7/1978 | Fed. Rep. of Germany | 206/5.1 |
| 0121818 | 5/1989 | Japan | 15/214 |
| 8501193 | 3/1985 | World Int. Prop. O. | 206/5.1 |

Primary Examiner—Steven A. Bratlie
Attorney, Agent, or Firm—Lonnie R. Drayer; Donald O. Nickey

[57] ABSTRACT

A device for cleaning contact lenses is disclosed which has a tubular or pen-like reservoir having an abradant tip having an external surface which is complementary to the general shape of a surface of a contact lens. A lens support member for supporting a contact lens during the cleaning process is also disclosed.

2 Claims, 1 Drawing Sheet

CONTACT LENS CLEANING SYSTEM

TECHNICAL FIELD

The present invention is directed to a device for cleaning contact lenses.

BACKGROUND OF THE INVENTION

Many people currently utilize soft contact lenses. These lenses must be cleaned regularly to avoid eye irritation and bacterial contamination.

Present methods of cleaning contact lenses have a variety of disadvantages. For example, lenses are often cleaned by rubbing them against the skin of the user's hand or hand-held cloth. This can damage or scratch the lens and may also result in additional buildup of oil on the lens due to the natural oiliness of the skin. Improper cleaning can also result in corneal infection.

Accordingly, it is one aspect of the present invention to provide a device for cleaning contact lenses that overcomes the above mentioned disadvantages of the prior art contact lens cleaning techniques and devices.

SUMMARY OF THE INVENTION

There is disclosed herein a device for cleaning contact lenses that comprises a tubular pen-like reservoir for lens cleaning solution and a porous abradant tip having an external surface that is complementary with a surface of a contact lens.

There is also disclosed herein a device for cleaning contact lenses wherein the external surface of the abradant tip is concave or convex.

More particularly, the present invention is directed to a device for dispensing soft contact lens cleaning solution and cleaning contact lenses. The dispenser has a pen-like configuration and has a rigid foam or similar porous abradant tip that is generally shaped to be complementary to the contour of a contact lens. In use, the contact lens is placed on a convex or concave shaped lens support and the abradant tip contacts the surface of the lens to be cleaned. The tubular reservoir is then activated by squeezing, capillary action or other means to release a small quantity of cleaning solution to the cleaning surface of the abradant tip and the device is rotated to impart an abrasive cleaning action to the contact lens surface.

The procedure of cleaning contact lenses using the device disclosed herein is more efficient than prior art procedures because it combines an integral dispensing means for lens cleaning solution with a mildly abrasive action which is contoured to fit the surfaces of the soft contact lenses.

DETAILED DESCRIPTION OF THE INVENTION

Figure 1:
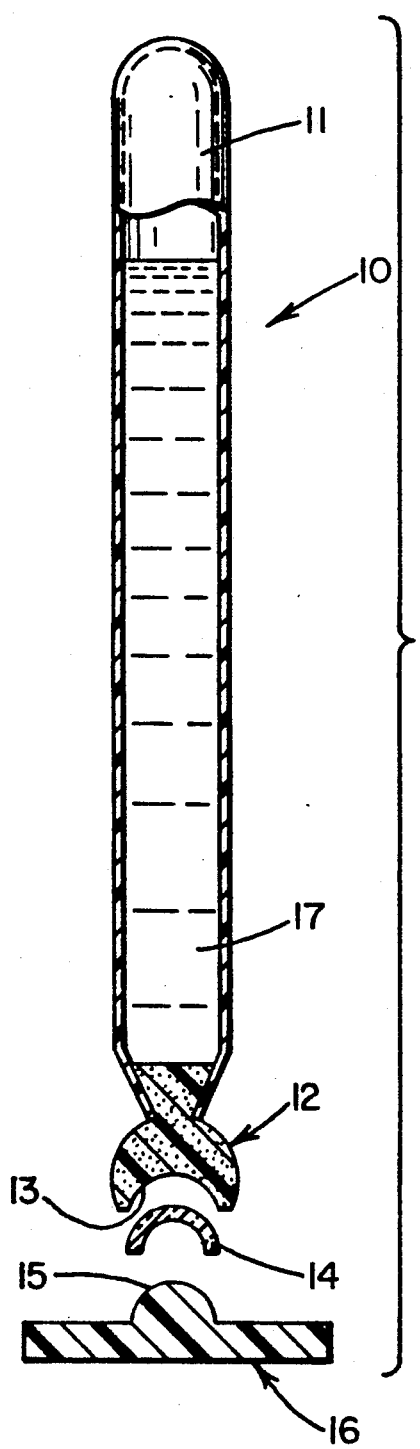
FIG. 1 is a simplified side plan view, partially broken away, of an embodiment of the present invention.

Referring to the drawings, FIG. 1 is a simplified side plan view, partially broken away, of an embodiment of the device 10 of the present invention. The device 10 includes a tubular pen-like reservoir 11 containing lens cleaning solution 17, and a porous abradant tip 12 attached to the reservoir and having a concave external surface 13 that is in the general shape of the outer surface of a soft contact lens 14. That is to say, an outer surface 13 of the abradant tip 12 is substantially complementary to a surface of a contact lens 14. The lens 14 is placed on a substantially complementary convex protrusion 15 of support 16 which is shaped to hold the lens in its natural contour. The device 10 may be activated by squeezing the flexible walls of the reservoir 11 to release lens cleaning solution 17 to the porous abradant tip 12 which is then brought into contact with the external surface of the contact lens 14. The device 10 may be rotated to impart a mildly abrasive cleaning action to the surface of the lens. If necessary the lens may also be immersed in a suitable solution to complete the cleaning and lens care process.

Figure 2:
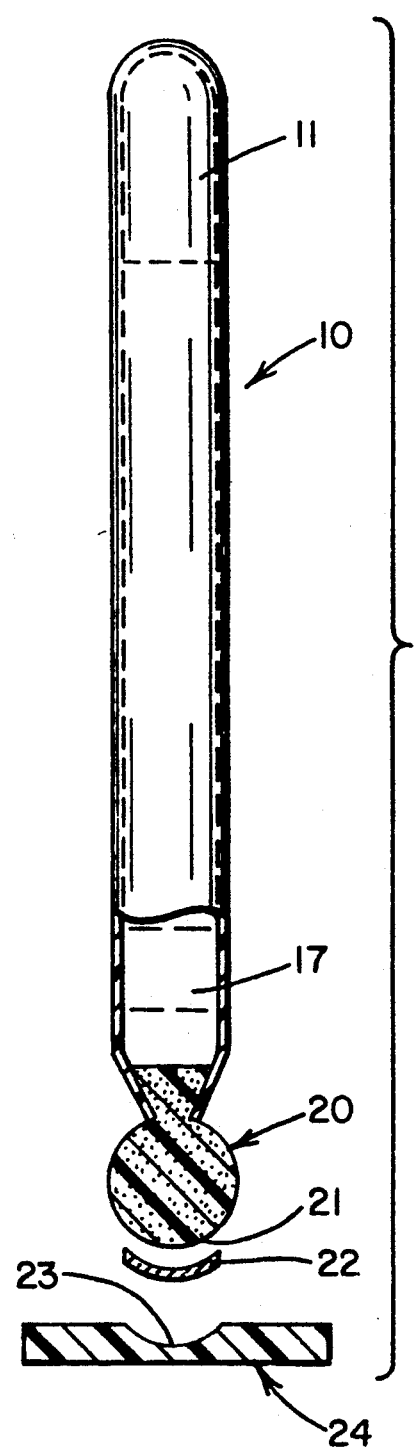
FIG. 2 is a simplified side plan view, partially broken away, of a second embodiment of the present invention.

FIG. 2 is a simplified side plan view, partially broken away, of a second embodiment of the device of the present invention. This embodiment differs from the embodiment shown in FIG. 1 in that the abradant tip 20 has a convex external surface 21 that is in the general shape of the inner surface of a soft contact lens 22. The lens 22 is placed in a concave indentation 23 of a support 24 and the device 10 is utilized as explained above.

The reservoir 11 may be constructed of any flexible plastic material such as polyester, silicones, polyurethane and the like, so long as it is inert with the contact lens cleaning solution 17. The abradant tip 12 may be constructed of any suitable low density semi-rigid foam material such as styrofoam, polyethylene, a urethane foam and fabric combination, etc. which is inert with the contact lens cleaning solution. Put another way, the abradant tip 12 should comprise a "sponge-like" material which is rigid enough to be mildly abrasive with respect to a contact lens. Most preferably, the abradant tip comprises a material which is pliable enough to be force fit into the opening in the reservoir in the manner illustrated in the drawing figures. Conventional lens cleaning solutions may be utilized.

Support members 16 and 24 may be separate tables or blocks or may be incorporated into a single block of a suitable inert plastic or other material.

While the embodiments shown in FIGS. 1 and 2 may be manufactured and sold individually, they may also be provided as a system for cleaning contact lenses which includes two reservoirs, both concave and convex abradant tips, and a support, or supports, providing a concave indentation and a convex protrusion.

The invention has been described in detail with particular reference to certain preferred embodiments thereof, but it should be understood that variations and modifications can be effected within the spirit and scope of the invention.

What is claimed is:

1. A system for cleaning contact lenses comprising:
   (a) a first device comprising a tubular reservoir containing lens cleaning solution and having a porous abradant tip attached thereto, said tip having an external surface which is concave, said reservoir comprising a flexible plastic material which is inert with said contact lens cleaning solution, said tip comprising a low density semi-rigid foam material selected from the group consisting of styrofoam, polyethylene and a urethane foam and fabric combination;
   (b) a second device comprising a tubular reservoir containing lens cleaning solution and having a porous abradant tip attached thereto, said tip having an external surface which is convex, said reservoir comprising a flexible plastic material which is inert with said cotnact lens cleaning solution, said tip comprising a low density semi-rigid foam material selected from the group consisting of styrofoam, polyethylene and a urethane foam and fabric combination;

(c) a lens support member having a convex protrusion for supporting a contact lens; and (d) a lens support member having a concave indentation for supporting a contact lens.

2. A system for cleaning contact lenses as described in claim 1 comprising only a single lens support member which has both a convex protrusion for supporting a contact lens and a concave indentation for supporting a contact lens.

* * * * *

UNITED STATES PATENT AND TRADEMARK OFFICE
CERTIFICATE OF CORRECTION

PATENT NO. : 5,071,276
DATED : December 10, 1991
INVENTOR(S) : Randolph D. Nielsen, Gerald W. Hietala, and Clarence J. Endicott It is certified that error appears in the above-identified patent and that said Letters Patent is hereby corrected as shown below: TITLE PAGE:

Field [75] "Clarence J. Endicotti" to --Clarence J. Endicott--

Column 3 Line 2 "cotnact" to --contact--

Signed and Sealed this

Thirteenth Day of April, 1993

Attest:

STEPHEN G. KUNIN

*Attesting Officer*  Acting Commissioner of Patents and Trademarks